US010869194B2

(12) United States Patent
Sones (10) Patent No.: US 10,869,194 B2
(45) Date of Patent: Dec. 15, 2020

(54) DEVICES, SYSTEMS, AND PROCESSES FOR AUTHENTICATING DEVICES (71) Applicant: DISH Network L.L.C., Englewood, CO (US)

(72) Inventor: Nathan Sones, Cheyenne, WY (US)

(73) Assignee: DISH Network L.L.C., Englewood, CO (US)

(*) Notice: Subject to any disclaimer, the term of this patent is extended or adjusted under 35 U.S.C. 154(b) by 312 days.

(21) Appl. No.: 15/853,329

(22) Filed: Dec. 22, 2017

(65) Prior Publication Data
US 2019/0200222 A1 Jun. 27, 2019

(51) Int. Cl.
*H04W 12/06* (2009.01)
*G06F 21/36* (2013.01)
*H04L 29/06* (2006.01)
*H04L 9/30* (2006.01)
*H04L 29/08* (2006.01)
*H04W 76/11* (2018.01)
*G06K 9/00* (2006.01)
(Continued)

(52) U.S. Cl.
CPC ............ *H04W 12/06* (2013.01); *G06F 21/36* (2013.01); *G06K 9/00006* (2013.01); *G06K 9/00221* (2013.01); *H04L 9/0825* (2013.01); *H04L 9/30* (2013.01); *H04L 9/3226* (2013.01); *H04L 63/0428* (2013.01); *H04L 67/20* (2013.01); *H04W 4/80* (2018.02); *H04W 64/003* (2013.01); *H04W 76/11* (2018.02); *A61B 5/02438* (2013.01); *A61B 5/083* (2013.01)

(58) Field of Classification Search
CPC ..... H04W 4/80; H04W 76/11; H04W 64/003; H04L 9/0825; H04L 9/30; H04L 9/3226; H04L 63/0428; H04L 67/20
See application file for complete search history.

(56) References Cited

U.S. PATENT DOCUMENTS 8,117,458 B2 * 2/2012 Osborn, III ............. G06F 21/36
713/183
8,533,475 B2 9/2013 Frikart et al.
(Continued)

OTHER PUBLICATIONS

Rainhard D. Findling, "Towards Device-to-User Authentication: Protecting Against", "https://usmile.at/sites/default/files/publications/Findling_15_TowardsDeviceto.pdf", 2015, pp. 1-5, Publisher: ACM.

*Primary Examiner* — Venkat Perungavoor
*Assistant Examiner* — Devin E Almeida
(74) *Attorney, Agent, or Firm* — Wash Park IP Ltd.; John T. Kennedy (57) ABSTRACT

Devices, systems and process for authenticating devices are described. For at least one embodiment, a process for authenticating an IoT device with a hub to initiate an authenticated session, includes the operations of establishing an electronic data connection between an IoT device and a hub, sending an initial authentication signal including a cryptologic component and at least two perceptible components, receiving a responsive message secured by a cryptologic component and including a selection of at least one of the at least two perceptible components, determining whether the selection includes the identifying perceptible component, and establishing an authenticated session between the hub and the IoT device, if the result of the determining step is affirmative.

18 Claims, 3 Drawing Sheets

(51) Int. Cl.
*H04W 4/80* (2018.01)
*H04W 64/00* (2009.01)
*H04L 9/08* (2006.01)
*H04L 9/32* (2006.01)
*A61B 5/024* (2006.01)
*A61B 5/083* (2006.01)

(56) References Cited

U.S. PATENT DOCUMENTS

| | | |
|---|---|---|
| 8,640,227 B2 | 1/2014 | Taxier et al. |
| 9,189,901 B2 | 11/2015 | Agrafioti et al. |
| 9,326,091 B2 | 4/2016 | Donnellan et al. |
| 9,363,108 B2 | 6/2016 | Bell et al. |
| 9,552,465 B2 | 1/2017 | Pike |
| 10,230,522 B1 * | 3/2019 | Roths .................... H04L 9/0833 |
| 10,291,477 B1 * | 5/2019 | Askar ...................... H04W 4/50 |
| 2004/0030934 A1 * | 2/2004 | Mizoguchi .............. G06F 21/36 726/18 |
| 2004/0073795 A1 | 4/2004 | Jablon |
| 2010/0043062 A1 * | 2/2010 | Alexander ............... G06F 21/36 726/6 |
| 2010/0287382 A1 | 11/2010 | Gyorffy et al. |
| 2012/0209749 A1 | 8/2012 | Hammad et al. |
| 2015/0334554 A1 * | 11/2015 | Song ...................... H04W 8/183 455/558 |
| 2015/0349966 A1 * | 12/2015 | Dimitrakos ........... H04L 9/3271 713/168 |
| 2016/0028715 A1 | 1/2016 | Sivashanmugam et al. |
| 2016/0066184 A1 | 3/2016 | Bhargav-Spantzel et al. |
| 2016/0373418 A1 * | 12/2016 | Stahl ...................... H04L 9/0838 |
| 2017/0041296 A1 | 2/2017 | Ford et al. |
| 2017/0083690 A1 * | 3/2017 | Fischer .................... H04L 63/10 |
| 2017/0022799 A1 | 8/2017 | Lee et al. |

* cited by examiner

DEVICES, SYSTEMS, AND PROCESSES FOR AUTHENTICATING DEVICES

TECHNICAL FIELD

The technology described herein generally relates to devices, systems, and processes for authenticating devices for interconnection to one or more networks. More specifically, the various embodiments disclosed generally relate to authenticating Internet-of-Things (IoT) devices for interconnection to one or more networks via a hub.

BACKGROUND

With the explosion of interconnected devices, such as IoT devices and other peripheral devices (hereafter individually and collectively, "IoT devices"), a need exists for reliable, secure and efficient mechanisms for connecting such IoT devices to one or more network data sources or other data locations. Often today, standalone devices or similar "all-in-one" devices, such as smartphones, personal data assistants, and similar devices are used to connect IoT devices to networked data sources or other data locations. Per such standard approach, each IoT device is individually managed, configured, connected, and secured to the "all-in-one" device (hereafter, a "primary device"). Technologies such as Bluetooth and others facilitate some of these tasks and allow primary devices to have one or more IoT devices connected thereto. Yet, there remains a need for a simplified mechanism for interconnecting, using, authenticating, securing, and managing IoT devices.

Further, primary devices are often expensive, bulky, and present unique concerns when one seeks to connect with IoT devices. By providing multiple functions and often configured as catch-all device, primary devices often present unique concerns with size, disruption to daily routines, power concerns, security concerns, and other concerns. These concerns of limit a primary device's capabilities to those supported by a given make, model, or version of a device. Often one is stuck with the built-in features, such as cameras, processors, and others that prohibit adaptation of a primary device to unique needs, uses, or wants.

Further, protocols for connecting primary devices and IoT devices often vary by both the primary device and the IoT device. These protocols often involve the use of varying authentication processes, including authentication processes requiring the participation of third parties. Each IoT device user may also be required to know and use unique passwords, protocols, or other features that present obstacles to the easy use of IoT devices with networked data sources or data locations. These concerns and others present unneeded challenges to use and integration of IoT devices in everyday use, as a user is often tied to their primary device for connectivity to data sources and data locations. Accordingly, devices, systems, and processes are needed which facilitate the interconnection of IoT devices with data sources and/or data locations without requiring the use of an "all-in-one" device.

SUMMARY

The various embodiments of the present disclosure relate in general to devices, systems, and processes for authenticating devices. In accordance with at least one embodiment of the present disclosure, a process for authenticating an IoT device with a hub to initiate an authenticated session includes the operation of establishing an electronic data connection between an IoT device and a hub. The process may also include the operation of sending an initial authentication signal. For at least one embodiment, the initial authentication signal may include a cryptologic component. For at least one embodiment, the initial authentication signal may include at least two perceptible components. At least one of the at least two perceptible components may include an identifying perceptible component. The process may also include receiving a responsive message. The responsive message may be secured prior to transmission by the IoT device. The responsive message may be secured by the cryptologic component. The responsive message may include a selection of at least one of the at least two perceptible components. For at least one embodiment, the process may include the operation of determining whether the selection includes an identifying perceptible component. For at least one embodiment, when the selection includes the identifying perceptible component, the process may include the operation of establishing an authenticated session between the hub and the IoT device.

For at least one embodiment, a process for authenticating an IoT device with a hub may include the operation of establishing an electronic data connection by Bluetooth pairing an IoT device with a hub.

For at least one embodiment, a process for authenticating an IoT device with a hub may include use of a cryptologic component that includes a public key of a public key-private key keychain. For at least one embodiment, at least one of two perceptible components may include at least one of an icon, a keyword, a sound, and a vibration. For at least one embodiment, at least two perceptible components may be used and include at least two icons. For at least one embodiment, a responsive message may include a combination of a unique identifying icon and a unique identifying keyword. For at least one embodiment, a unique identifying icon may be selectable from the at least two icons.

For at least one embodiment, a process for authenticating an IoT device with a hub may include use of a unique identifying keyword that is communicated to an IoT device in an initial authentication signal. For at least one embodiment, the process may include receiving device user identifying data. The device user identifying data may identify an intended user of an IoT device for a session. For at least one embodiment, a process for authenticating an IoT device with a hub may include determining whether an intended user is authorized for the session. For at least one embodiment, the operation of determining whether an intended user is authorized for a session may include the operation of contacting a user verification data service. For at least one embodiment, user identifying data may be secured, prior to transmission by an IoT device, using a cryptologic component.

For at least one embodiment, a process for authenticating an IoT device with a hub may include use the operation of providing, during the authenticated session, a communications link connecting an IoT device with a third-party service provider. For at least one embodiment, when a communications link is established, data can be communicated between a third-party service provider and an IoT device. For at least one embodiment, data may be communicated between a third-party service provider via a device link between a hub and an IoT device. For at least one embodiment, a hub link between a hub and a third-party service provider may be utilized. For at least one embodiment, a device link may be utilized during an authenticated session.

For at least one embodiment, a process for authenticating an IoT device with a hub may include communicating with a service provider. For at least one embodiment, the service provider may be at least one of a web services provider, a streaming service provider, and a data service provider. For at least one embodiment, the service provider may be a third-party service provider.

For at least one embodiment, a process for authenticating an IoT device with a hub may include the operation of establishing a second hub link between a hub and a second third-party service provider. For at least one embodiment, the process may include establishing a second device link between an IoT device and a hub. For at least one embodiment, the second device link may facilitate a second authenticated session.

For at least one embodiment, a device for use in authenticating an IoT device with a hub may include use of a hub device configured for use in establishing an authenticated session with an IoT device. For at least one embodiment, a hub device may include a processor configured to execute computer readable instructions for establishing an authenticated session between a device and an IoT device. For at least one embodiment, the hub device may include an input/output module. The input/output module may be coupled to the processor. For at least one embodiment, the hub device may include a security module. The security module may be coupled to the processor. For at least one embodiment, the hub device may include a communications module. The communications module may be coupled to the processor. For at least one embodiment, the hub device may include a storage module. The storage module may be coupled to the processor. The storage module may be configured to store computer readable instructions.

For at least one embodiment, a hub device may include computer readable instructions for performing the operation of establishing an electronic data connection between an IoT device and the hub device. The electronic data connection may be established, at least in part, using a communications module. For at least one embodiment, the instructions may include those for performing the operation of sending, via the communications module, an initial authentication signal. For at least one embodiment, the initial authentication signal may include a cryptologic component generated by the security module. For at least one embodiment, the initial authentication signal may include two or more perceptible components. For at least one embodiment, the initial authentication signal may include at least two perceptible components. For at least one embodiment, at least one of two or more perceptible components is an identifying perceptible component.

For at least one embodiment, a hub device may include computer readable instructions for performing the operation of receiving a responsive message. The responsive message may be received using a communications module. The responsive message may be secured, prior to transmission by the IoT device. A cryptologic component may be used to secure the responsive message. For at least one embodiment, the responsive message may include a selection of at least one of the at least two perceptible components.

For at least one embodiment, a hub device may include computer readable instructions for performing the operation of decrypting a responsive message. The responsive message may be decrypted using a security module.

For at least one embodiment, a hub device may include computer readable instructions for performing the operation of determining whether a selection includes an identifying perceptible component. For at least one embodiment, a processor may be configured to perform the determining operation. For at least one embodiment, a hub device may include computer readable instructions for performing the operation of establishing an authenticated session between the hub device and the IoT device when a positive result is obtained from the determining operation. For at least one embodiment, a hub device may include computer readable instructions for performing the operation of outputting a humanly perceptible signal indicating the authenticated session is established when a positive result is obtained from the determining operation. The humanly perceptible signal may be output using an input/output module.

For at least one embodiment, a hub device may include a coupling module configured to couple an external device to the hub device. For at least one embodiment, the coupling module may use at least one of physical coupling, magnetic coupling, inductive coupling, electrical coupling, and electro-optical coupling.

For at least one embodiment, a hub device may include at least one of a power source, a second input/output module, a mapping module, a streaming module, a second processing module, a second data storage module, a sensing module.

For at least one embodiment, a hub device may include a position module, coupled to the processor, and configured to determine a position of the hub device.

For at least one embodiment, a hub device may include a sensor module, coupled to the processor, and configured to monitor at least one biometric for a user of the hub device and output at least one sensed signal indicative of the monitored biometric.

For at least one embodiment, a hub device may include computer readable instructions for performing the operation of receiving, from a sensor module, at least one sensed signal. For at least one embodiment, a hub device may include computer readable instructions for performing the operation of analyzing the at least one sensed signal for an emergency medical condition. For at least one embodiment, a hub device may include computer readable instructions for performing the operation of detecting an emergency medical condition. For at least one embodiment, a hub device may include computer readable instructions for performing the operation of establishing, using the communications module, a communications link with a first-responder. For at least one embodiment, a hub device may include computer readable instructions for performing the operation of communicating to a first-responder a current position, and at least one sensed signal.

For at least one embodiment, a non-transitory processor-readable medium providing processor-readable instructions configured to cause one or more processors to execute an application program for use in establishing an authenticated session between a hub and an IoT device is described. For at least one embodiment, the processor-readable instructions may include instructions for execution by a processor in an IoT device. For at least one embodiment, the instructions may include establishing an electronic data connection between the IoT device and the hub. For at least one embodiment, the instructions may include receiving from the hub an initial authentication signal. For at least one embodiment, the initial authentication signal may include a cryptologic component and at least two perceptible components. For at least one embodiment, at least one of the at least two perceptible components is an identifying perceptible component.

For at least one embodiment, the processor-readable instructions may include outputting a responsive message secured by the cryptologic component. For at least one embodiment, the processor-readable instructions may include a selection, by a user of the IoT device, of at least one of the at least two perceptible components.

For at least one embodiment, the processor-readable instructions may include requesting session data from at least one of the hub and a third-party service provider via the authenticated session between the hub and the IoT device. The session data may be requested upon determining that the responsive message includes a selection of the identifying perceptible component. The determining may be accomplished by a hub.

For at least one embodiment, the processor-readable instructions may include establishing an authenticated session between a hub and an IoT device. For at least one embodiment, session data may include data provided by at least one of a streaming video service provider, a web service provider, and a data service provider.

BRIEF DESCRIPTION OF THE DRAWINGS

The features, aspects, advantages, functions, modules, and components of the devices, systems and methods provided by the various embodiments of the present disclosure are further disclosed herein regarding at least one of the following descriptions and accompanying drawing figures. In the appended figures, similar components or elements of the same type may have the same reference number and may include an additional alphabetic designator, such as 108a-108n, and the like, wherein the alphabetic designator indicates that the components bearing the same reference number, e.g., 108, share common properties and/or characteristics. Further, various views of a component may be distinguished by a first reference label followed by a dash and a second reference label, wherein the second reference label is used for purposes of this description to designate a view of the component. When only the first reference label is used in the specification, the description is applicable to any of the similar components and/or views having the same first reference number irrespective of any additional alphabetic designators or second reference labels, if any.

DETAILED DESCRIPTION

The various embodiments described herein are directed to devices, systems, and processes for providing connection by IoT devices to data sources and/or data locations, such as those reachable via one or more data networks, without requiring the use of a primary device, such as a smartphone or PDA, by using a hub device. In accordance with at least one embodiment of the present disclosure a hub device provides the minimal capabilities needed to facilitate connections of itself and IoT devices to networked data sources and data locations. Acting as a stand-alone device, the hub may be configured to provide connectivity for high usage tasks, such as voice dialing, voice texting, interaction with voice-based searching services, bio-medical reporting, emergency services, and others. Acting as a pass-through device, the hub may be configured to facilitate connectivity by one or more IoT devices with one or more networked data sources and/or data locations. Examples of such connectivity may include the providing of streaming video services to an IoT device, where the IoT device provides the hardware and software necessary to present videos and other audio/video content to one or more viewers and the hub facilitates connecting of the IoT device with a networked data streaming service. Acting as a pass-through device, the hub may be paired with any desired IoT device to provide any desired functionality. Thus, unlike today's primary devices, the hub does not require the functionality, in and by itself, to provide any desired data, function, feature, service, or otherwise (hereafter individually and collectively, "services"). Instead, such the data networking, authentication, and connectivity elements used in the providing of services are facilitated by the hub, while the actual providing of such services is facilitated by the IoT device communicatively coupled to the hub.

Figure 1:
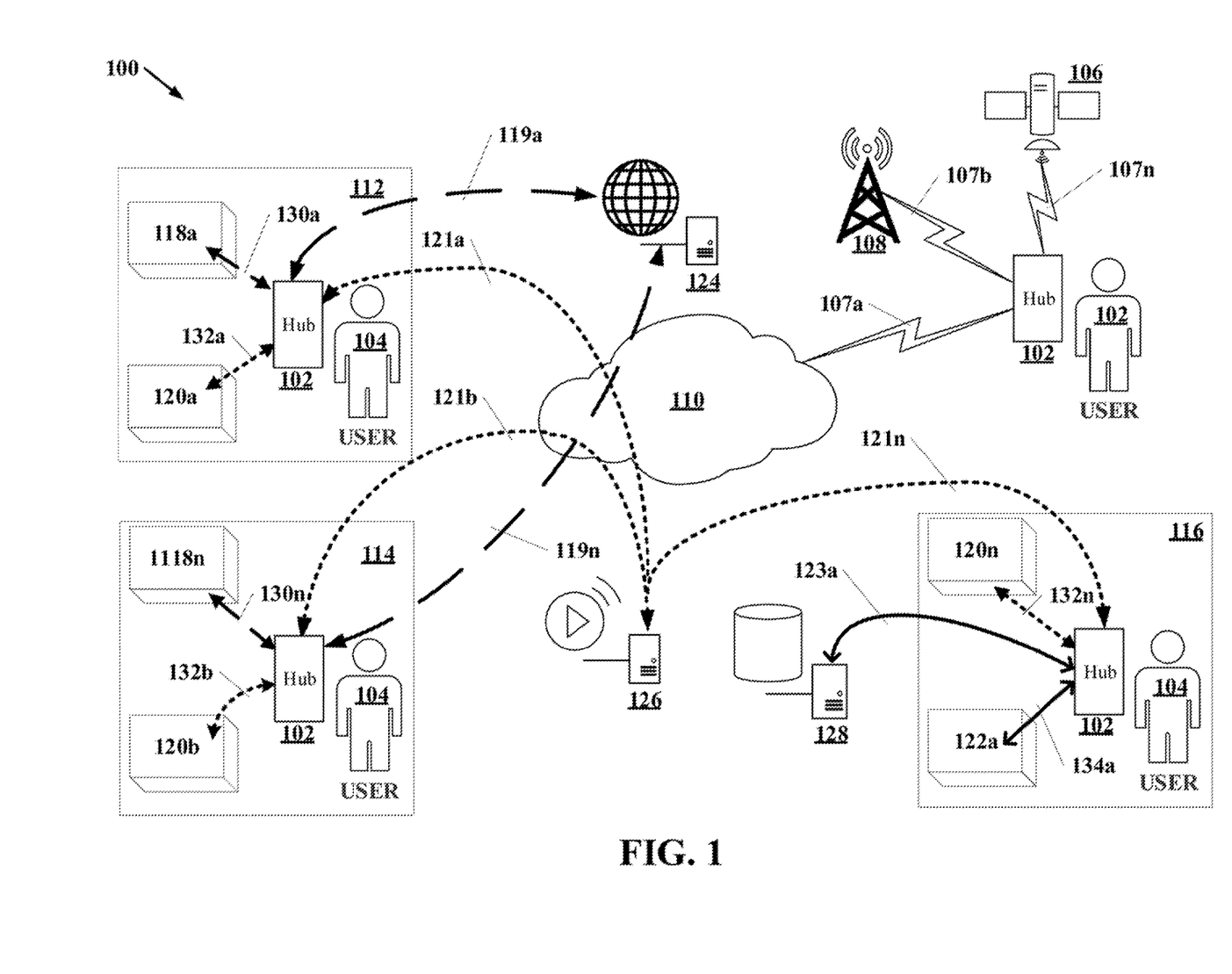
FIG. 1 is schematic representation of a system for connecting one or more devices to a networked data source or other data location using a hub and in accordance with at least one embodiment of the present disclosure.

As shown in FIG. 1, one embodiment of a system 100 for providing stand-alone and pass-through device capabilities includes a hub 102. The hub 102 may be uniquely associated with and possessed by a person 104 (a "hub user"). The hub 102 may be configured in a form factor convenient to everyday wear, in practically any environmental condition, such as a watch, a pod (e.g., a shoe pod), a medallion, a badge (magnetically, or otherwise attached to a user's clothing), embedded in the person, or otherwise. When configured as a watch for at least one embodiment, the hub 102 may be configured for attachment to the user using anti-bacterial materials, such as bamboo wrist bands and otherwise. The hub 102 may be configured to provide stand-alone features and functions, such as the capability to provide voice services such as dialing, texting, searching, message playback, device control, and otherwise. Such voice services may be supported by connectivity by the hub 102 with one or more service providers, such as terrestrial services providers 108, network service providers 110, satellite service providers 106, and other service providers. It is to be appreciated that the hub 102 may be configured in stand-alone mode to provider connectivity to one or more service providers, and thereby to other third-party service providers, data sources, data locations, or otherwise using any known or later arising technologies and via one or more primary hub links 107a-n. Such primary hub links 107a-n may utilize any known or later arising communications and/or networking technologies.

As further shown in FIG. 1, the system 100 may include one or more IoT devices, such as one or more first IoT devices 118a-n, one or more second IoT devices 120a-n, one or more third IoT devices 122a, and otherwise. An IoT device is typically a device that is not physically connected to a hub for routine operations. For non-routine operations, such as maintenance, updating, and/or configuring of a hub, an IoT device may physically connected to a hub, if so desired for a given embodiment. The system 100 may be configured for any given embodiment to support the use of any desired type of IoT device. Such IoT devices may be configured for stand-alone use and/or use with one or more third-party services, features, functions, data, or otherwise. The particularities of the hardware and software, features and functions supported and provided by any given IoT device are limitless. In at least one embodiment, the user of the IoT device, the "device user" is the same as the hub user. In other embodiments, a device user may not be the hub user. In one or more embodiments, the device user may rely upon permissions from and/or rights associated with a hub user to use a given IoT device. For example, a child desiring to access streaming video services may rely upon the permissions of an adult hub user to use such services.

The system 100 may also be configured to support the interconnectivity of an IoT device, via a hub 102, with one or more third-party service providers. Non-limiting examples of such service providers may include web service providers 124, streaming service providers 126, and data service providers 128. The hub 102 provides connectivity between an IoT device and a service provider using one or more device communications links (virtual "spokes") between the IoT device and the hub 102, such as a $1^{st}$ spoke/device link 130a-n, $2^{nd}$ spoke/device link 132a-n, and Nth spoke/device link 134a-n, and via one or more secondary hub links 119a-n, tertiary hub links 121a-n, and one or more Nth hub links 123a.

For at least one embodiment, the hub 102 may be configured to act as a central connectivity point with one or more virtual "spokes" connecting to one or more IoT devices. For at least one embodiment, the one or more virtual "spokes" may exist as a data link between a given hub and one or more IoT devices at a given time. The virtual spokes may be connected, configured, used by a hub and/or an IoT device that is within communications range of a corresponding hub. Spokes may be disconnected, disabled, or otherwise configured when a hub is not within range of a given IoT device. Further, it is to be appreciated that the technologies, protocols, spectrum, and other elements used for a given spoke/device link may be the same or different from one IoT device to another. For example, an IoT device, such as the illustrative $2^{nd}$ IoT device 120a-n used for streaming video services may be configured to use a high bandwidth spoke/device link, whereas a $1^{st}$ IoT device 118a-configured to provide access to one or more web services, such as an online shopping service, a news feed service, or otherwise, may use a lower bandwidth spoke/device link.

Likewise, the technologies, protocols, spectrum, and other elements of a hub link may be the same or may vary from those used to support a device link—as needed and/or desired to support the features and functions provided by a given IoT device. Further, such hub link characteristics may vary in view of the connectivity options available to a given hub, at a given, time, location, user preferences, data environment, and otherwise. As shown in FIG. 1, a given hub link 107/119/121/123 may be configured and/or configurable to support a service desired by the hub in support of one or more IoT devices.

For at least one embodiment, IoT devices may also be configured to support a hub 102 in its stand-alone device configuration. For example, a first IoT device 118a-n may be configured to provide a display, mapping features and functions, and similar hardware and software used to facilitate use of the hub 102 as a direction providing unit, for example, a unit providing visual turn-by-turn directions while using built-in global positioning sensing/location sensing capabilities of a hub 102 so configured. Similarly, a second IoT device 120a-n may be configured, when video streaming services are desired, to provide a higher quality display while using primarily the pass-through capabilities of a hub 102. Likewise, an Nth IoT device 122a-n may be configured to access data from a network data source or location, such as data service provider 128. The IoT device may be configured to use both the stand-alone capabilities and the pass-through capabilities of a hub 102. The stand-alone capabilities may include, for example, security capabilities, while the pass-through capabilities may include, for example, the providing some or all of the data accessed from the data service provider 128 to the IoT device 122a-n in any desired form, including encrypted, unencrypted, or otherwise. Thus, it is to be appreciated that a hub 102 may be configured to support any desired combination or use of a given hub's stand-alone and pass-through capabilities in support of the features and functions to be provided by a given IoT device, at a given time, and in any given environment.

Figure 2:
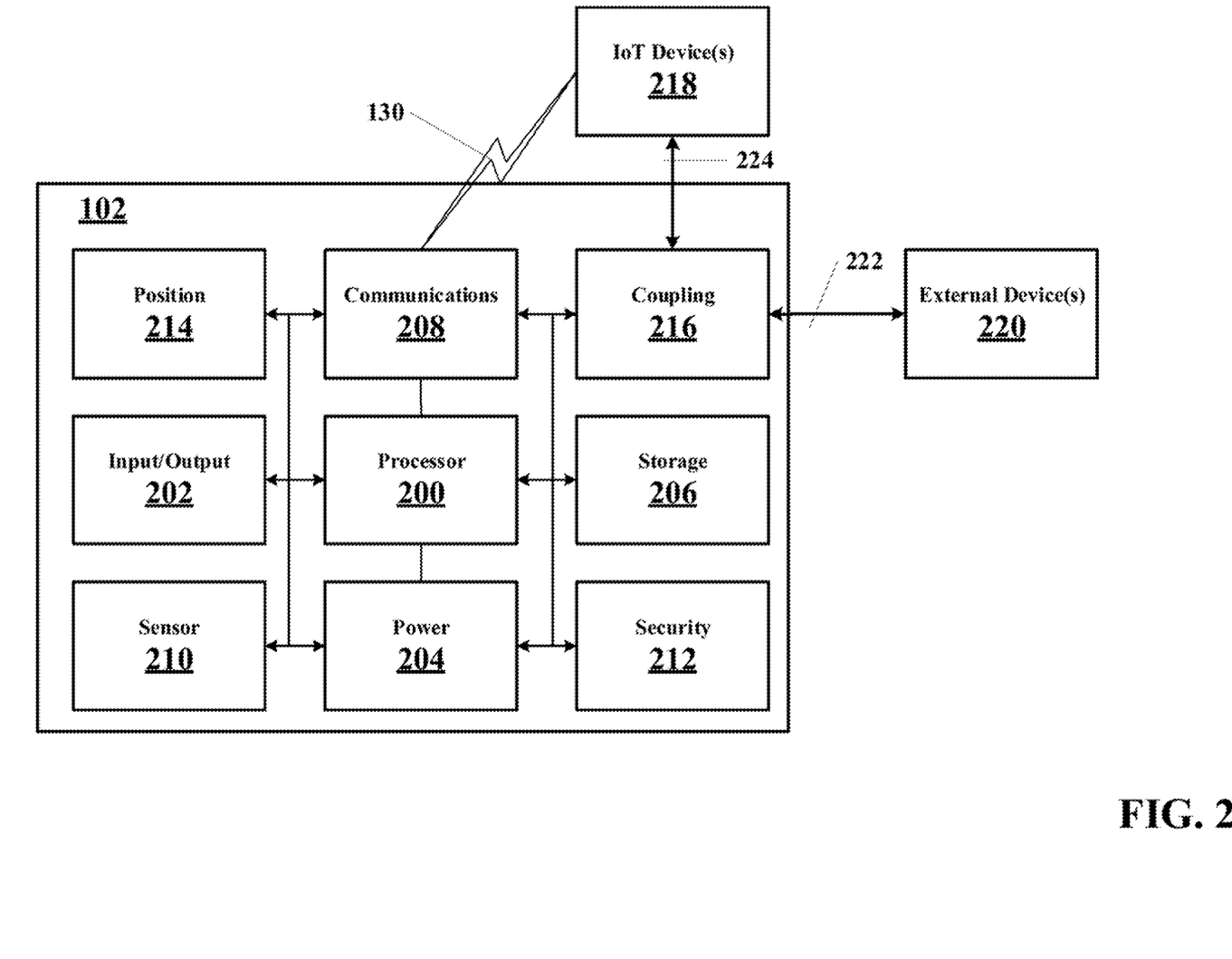
FIG. 2 is a schematic representation of a hub in accordance with at least one embodiment of the present disclosure.

As shown in FIG. 2 for at least one embodiment of the present disclosure, a hub 102 may include one or more of combinations of a processor 200, an input/output module 202, a power module 204, a storage module 206, a communications module 208, a sensor module 210, a security module 212, a position module 214, and a coupling module 216. Other modules or fewer modules may be used in other embodiments. The modules may be interconnected using known and/or later arising technologies. The processor 200 may be any known or later arising processor capable of providing and/or supporting the features and functions of a hub as needed for any given intended use of a hub and in accordance with one or more of the various embodiments of the present disclosure. For at least one non-limiting embodiment, the processor is configured as and/or has the capabilities of a 32-bit or 64-bit, multi-core ARM based processor. In at least one embodiment, the processor 200 is configured to support both stand-alone and pass-through capabilities.

For at least one embodiment, the processor 200 may be communicatively coupled to at least one input/output module 202 configured to facilitate interfacing with the user. The input/output module 202 may be configured to support audible interfacing with the user. The module 202 may be configured to support audible interfacing using natural language (e.g., commands and replies received and sent in a user's desired language), audible prompts (e.g., beeps, chimes, or the like), combinations of the foregoing, and otherwise. The module 202 may be configured to include known or later arising voice recognition technology and/or to access such technologies from one or more third-party service providers, such as via a hub link. The module 202 may include tactile input devices, such as buttons, capacitive or otherwise touch interfaces, or otherwise. The module 202 may include tactile output interfaces, such as elements that cause the hub to vibrate. Vibration patterns, frequencies, or otherwise may be utilized to provide different signaling to the user. The module 202 may be configured to include visual output devices, such as lights, visual displays, or otherwise. The module 202 may include features utilized to recognize a user, such as voice recognition, facial recognition, finger print recognition, biometric recognition, or otherwise.

The module 202 may include support for and/or be configured to support other forms of user interface, including IoT devices 218 supporting input/output messages between a user and a hub, such as the above mentioned visual display provided by an IoT device in support of direction providing services. Such IoT devices 218 may be communicatively coupled to the hub via a spoke/device link (for example, the first spoke/device link 130) and the communications module 208 (described further below). It is to be appreciated that a stand-alone mode of operation and a pass-through mode of operation may execute individually or substantially simultaneously, such as by use of multi-tasking, multi-threading, multi-core, or other processing hardware and/or software technologies.

The module 202 may include and/or be configured to support one or more external devices 220 supporting input/ output, sensing, position determining, communications, storage, or other features, functions or capabilities of a given hub. An external device 220 may be communicatively coupled to the hub 102 via the coupling module 216 and an external device link 222 (each described further below). Examples of external devices include, but are not limited to battery, digital watch face, analog watch face, touch screen, and camera. By use of IoT devices 218 and/or external devices 220, such input/output features and functions may vary over time for any given hub. For at least one non-limiting embodiment, the input/output module includes a microphone, a speaker and an input button. A depressing and/or holding of a button for various time periods, sequences or otherwise may be supported by an input/output module 202 and utilized by a user to control and/or change the operating status of a hub. Voice commands may be used to change and/or control the operating status of a hub. A shaking or sudden movement of a hub, or a change in a measured characteristic of a user, as detected for example, by a sensor module 210, may be utilized by an input/output module 202 to control and/or configure the operations of a hub. A change in location of a hub, for example, a movement of a hub a predetermined distance as determined for example by a position module 214, may be utilized by an input/output module 202 to control and/or configure the operations of a hub.

The hub may be configured to support operations in any desired environment, such as those arising in wet, dry, cold, hot, or otherwise. Accordingly, it is to be appreciated that the input/output module 202 may be configured, for any given embodiment, to support desired input and output features and functions for a hub and such features and functions may be augmented by use of IoT devices 218 and/or external devices 220.

As further shown in FIG. 2 and for at least one embodiment, a hub 102 may include an internal power module 204. The power module 204 may be configured using any known or later arising technology. For at least one embodiment, the power module 204 may include a battery having a desired rating in amp-hours, output voltage, output current, or combinations of the foregoing. The power module 240 may be provided in a small or reduced size form factor designed to support an operating time of one or more desired features or functions, with additional power being provided by an external device 220. The power module 204 may be recharged using any known or later arising technology including, but not limited to, inductive charging. The power module 204 may be configured for use with power sources provided in external devices 220. Such additional battery may be used to recharge, augment, or provide power in addition to the power source 204. An external device 220 may be configured to provide additional power while also providing one or more other features or functions, such as the above-mentioned input/output functions and/or other features or functions desired for a given embodiment.

For example, an external device 220 configured to support streaming video services may include the providing of power to the hub during a streaming session by an external power source physically coupled to the hub. Such power may be provided using an external device link 222. For at least one embodiment, an external device link 222 varies from a wired device link 224 with the former having a physical connection with a hub and the latter having a remote connection, via a wire or data cable, with a hub. Either of the external device link 222 or the wired IoT device link 224 may be used to provide power and data signals to a hub. Further, an IoT device may be wirelessly linked to a hub using a device link 130/132/134. For example, a wired connection between an IoT device and a hub may be provided over an IoT device link 224, while a wireless connection may be provided over a device link 130/132/134. A given IoT device may be configured to support use of either type of link, wired or wireless. For at least one embodiment, the wired device link 224 and the device link 130/132/134 may be configured as a single link, wired, wireless, inductive, or otherwise between a remote device 218 and a hub 102. Accordingly, the links used between an IoT device and a hub are collectively referred to herein as a "device link" with it being appreciated that a wired device link may be configured to additionally provide power to a hub in addition to data. For at least one embodiment, an external device 220 may include a battery or power source.

As further shown in FIG. 2 and for at least one embodiment, a hub 102 may include a storage module 206. The storage module 206 may be configured using any known or later arising data storage technologies. In at least one embodiment, the storage module 206 may be configured using flash memory technologies. For at least one embodiment, the storage module 206 may be configured using micro-SD card technology. The storage module 206 may be configured to have any desired data storage size, read/write speed, redundancy, or otherwise. The storage module 206 may be configured to provide temporary/transient and/or permanent/non-transient storage of one or more data sets. Such data sets may include firmware and software instructions, and data for use in operating the hub 102. Such data sets may include software instructions configured for execution by the processor, another module of the hub 102, an external device 220, an IoT device 218, or otherwise. Such software instructions provide computer executable operations that facilitate one or more features or functions of a hub, an IoT device, an external device, or otherwise. The storage module 206 may be configured to operate in conjunction with network storage devices and servers, IoT devices, external devices, and otherwise. For at least one embodiment, the storage module 206 may be configured to store one more data sets utilized to authenticate a user 104 with one or more providers. These and other data sets may be encrypted using known or later arising technologies.

As further shown in FIG. 2 and for at least one embodiment, a hub 102 may include a communications module 208. The communications module 208 may be configured to utilize any known or later arising technology to establish, maintain, and operate one or more hub links 107/119/121/123, device links 130/132/134, external device links 222, and/or wired IoT device links 224. Examples of technologies that may be utilized with one or more embodiments include, but are not limited to, Bluetooth, ZigBee, Near Field Communications, WIFI, 3G, 4G, 5G, cellular, and others. The communications module 208 may be configured to include one or more data ports for establishing connections between a hub and another device, such as a laptop computer. Such data ports may support any known or later arising technologies, such as USB 2.0, USB 3.0, Ethernet, Firewire, HDMI, and others. The communications module 208 may be configured to support the transfer of data formatted using any desired protocol and at any desired data rates/speeds. The communications module 208 may be connected to one or more antennas (not shown) to facilitate wireless data transfers. Such antenna may support short-range technologies, such as 802.11a/c/g/n and others, and/or long-range technologies, such as 4G, 5G, and others. The communications module 208 may be configured to communicate signals using terrestrial systems, space based systems, and combinations thereof systems. For example, a hub 102 may be configured to receive GPS signals from a satellite.

As further shown in FIG. 2 and for at least one embodiment, a hub 102 may include a sensor module 210. The sensor module 210 may include one or more biometric, environmental, or other sensors. For at least one embodiment, a hub 102 may be configured to directly sense one or more of a user's biometrics, such as heartrate. Sensors may be configured for contact with a user's skin facing. For at least one embodiment, a hub may be configured to placement on a user's body to provide contact with a user's body to facilitate biometric sensing of one or more of such user's body functions. For at least one embodiment, a hub 102 may be configured to receive biometric signals, environmental signals, or other sensed signals (hereafter, individually and collectively "sensed signals"), via the communications module 208, where such sensed signals may be obtained using an IoT device 218 and/or an external device 220. Such signals may be received using a wireless device link 130/132/134 and/or a wired device link 224. A hub 102 may be configured to utilize one or more sensed signals to monitor a user's current condition, such as a heart rate, respiratory rate, blood pressure, or otherwise. A hub 102 may be configured, based on such sensed signals, to take one or more actions, such as notifying emergency services when a cardiac event is sensed. A hub 102 may be configured to activate one or more components of an input/output module 202 based upon sensed signals. For example, when a user is having a cardiac event, as indicated by one or more sensed signals, a microphone and speaker may be activated, along with a GPS, and communications module, such that voice, location, heart rate and other information can be communicated to emergency responders. It is to be appreciated that any type of known or later arising sensor technologies may be used in conjunction with one or more embodiments of the present disclosure. Such sensing technologies may be provided in a hub, in an external device and/or in an IoT device.

As further shown in FIG. 2 and for at least one embodiment, a hub 102 may include a security module 212 configured to include hardware and/or software which facilitates secure storage, processing, authentication, and communications of data between a hub 102, an IoT device 218, a service provider, an external device 220, and otherwise. For at least one embodiment, a security module 212 may be configured to support the use of private and public encryption keys. Any known or later arising data security technologies may be used in and/or with security module 212. Security module 212, in conjunction with storage module 206 may be configured to securely store a user's authentication credentials, preferences, passwords and otherwise used to access service providers. It is to be appreciated that the security module 212 may be configured, in conjunction with the sensor module 210, to "lock" or "unlock" (i.e., provide access to or deny access to) one or more features and/or functions of a hub, an IoT device, an external device, and/or a service provider based upon biometric signatures, such as heart rhythms, gait profiles, or otherwise.

As further shown in FIG. 2 and for at least one embodiment, a hub 102 may include a position module 214. The position module 214 may include the use of known or later arising positional, attitudinal, rotational, or other location and/or movement determining and/or sensing technologies. Non-limiting examples of such technologies include the use of GPS signals for position determinations. The use of wireless signal triangulations for position determinations may be supported by position module 214, where such wireless signal triangulations may arise using public networks, private networks, or otherwise. Movement sensors, such as accelerometers, rotational sensors, and others may be supported by a position module 214. Such position, location and similar sensors being identified herein a "position sensors" and signals from such sensors as "position signals." As discussed above, position signals from one or more of such position sensors may be utilized to support one or more features and/or functions of a hub 102, an IoT device, a service provider, and/or an external device.

As further shown in FIG. 2 and for at least one embodiment, a hub 102 may include a coupling module 216. The coupling module 216 may include any desired type of connectivity devices for use in securing temporarily or for any duration up to and including permanently, an external device 220 to a hub 102. For at least one embodiment, the coupling module 218 may facilitate magnetic coupling of an external device 220 to a hub 102. For at least one embodiment, the coupling module 218 may facilitate the physical coupling, as distinguished from a data coupling, of an IoT device 218 to a hub. For at least one embodiment, the coupling module 218 may facilitate physical coupling via the use of Velcro, fastening sleeves, magnets, epoxies, or otherwise. For at least one embodiment, the coupling module 218 may facilitate both the physical coupling of an external device 220 and/or an IoT device 218 to a hub 102 as well as the communicative coupling of one or more of such devices. Such communicative coupling may occur electrically, inductively, electro-optically, or otherwise. For at least one embodiment, the coupling module 218 may be configured to provide electrical, physical, mechanical, and/or other isolation between a hub 102 and an external device 220 or IoT device 218 coupled thereto.

It is to be appreciated that any given embodiment of a hub 102 may include one or more of the above described modules and/or other modules, as desired to support a given individual or set of IoT devices while in a pass-through mode of operation, while providing a desired set of core features and/or functions when operating in a stand-alone mode of operation.

Figure 3:
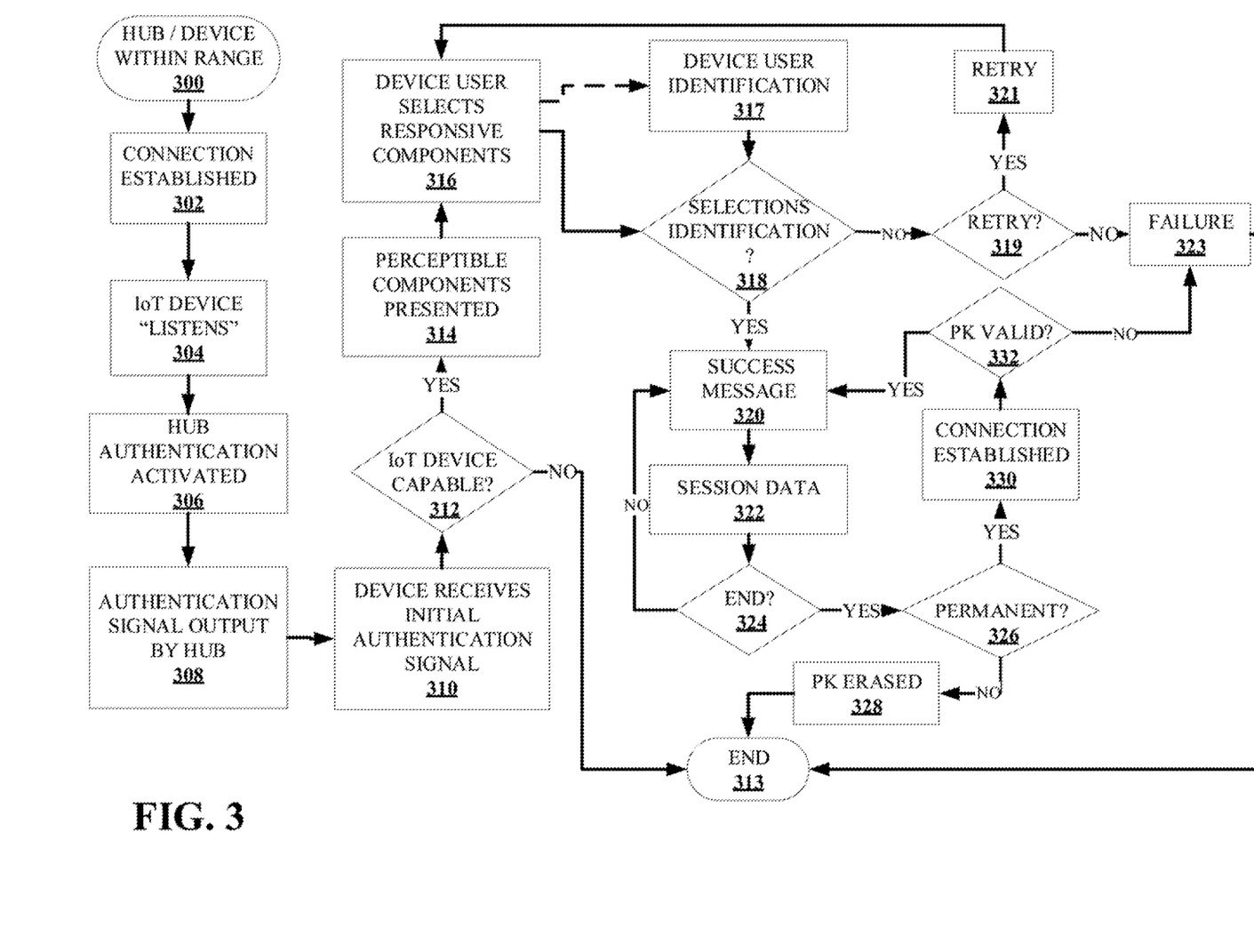
FIG. 3 is a flow chart depicting a process for interconnecting an IoT device with a hub in accordance with at least one embodiment of the present disclosure.

As shown in FIG. 3, a process for establishing a connection between a hub 102 and an IoT device begins when a hub 102 enters the communication range of an IoT device 218, and vice versa (Operation 300). It is to be appreciated that the hub 102, being commonly associated with a person, is typically mobile. However, an IoT device may also be mobile relative to a then stationary hub. For at least one embodiment, where a hub 102 is configured to communicate with IoT devices 218 using short-range communications protocols, such as Bluetooth, the hub 102 and IoT device 218 enter communications range when they are within a few dozen feet of each other. Further, it is to be appreciated that intermediate range communications protocols, such as WIFI, may be used to establish communications between a hub 102 and an IoT device 218. Likewise, longer range communications protocols, such as 4G and 5G, may be used between a hub 102 and an IoT device. Accordingly, when Operation 300 may occur will typically depend upon one or more characteristics of a given IoT device and a given hub for a given implementation of an embodiment of the present disclosure.

Per Operation 302, upon a hub 102 and IoT device 218 entering (if not already being present) within range, a communications link or connection is established. It is to be appreciated that upon a first instance of a hub 102 and IoT device 218 begin within range, commonly known link establishment protocols may be used, such as Bluetooth pairing protocols. Likewise, for a hub and IoT device that have been previously connected, e.g., Bluetooth paired, such pairing protocols may or may not need to be repeated. It is to be appreciated that a given hub 102 may be paired, using one or more communications protocols, with one or more devices at any given time. Likewise, for at least one embodiment, a given IoT device may be paired with multiple hubs at any given time.

Per Operation 304, once the hub 102 and the IoT device 218 of interest at that time are "paired" or otherwise communicatively connected using a known or later arising pairing protocol, the process proceeds with the IoT device, such as the 1$^{st}$ Device 118a "listening" for an authentication signal sent by a paired hub 102. That is, unlike many prior art approaches where a device initiates authentication, per at least one embodiment of the present disclosure, initiation of an authentication process proceeds with a hub. It is to be appreciated that per this process, as described further below, the user, via the hub, controls and initiates when an authentication and whether an eventual exchange of data by and between a hub and a given IoT device is to occur.

Per Operation 306, upon receiving a user or other input to begin authentication, hub authentication is activated. Activation of hub authentication may occur based upon a depressing of an input button on a hub, based upon a biometric sensing, a positional sensing, a voice command, or otherwise. That is, activation of hub authentication may occur automatically, semi-automatically (e.g., based upon a sensed condition), or manually upon a user action requesting such authentication activation.

Per Operation 308, the hub outputs an initial authentication signal. In at least one embodiment, the initial authentication signal includes a public key. In at least one embodiment, the public key is a transient or temporary key having a pre-determined period for use. In at least one embodiment, the public key is non-transient.

In at least one embodiment, the initial authentication signal may also include, in addition to at least the public key, data for use by the receiving IoT device(s) to generate one or more icons for presentation to a user of the IoT device. The one or more icons may include a unique identifying icon. The one or more icons may be any configuration of graphical or other characters, arranged in any desired order, that are associable with a given hub. The identifying icon may have a temporary association or a permanent association with a given hub. The outputting of the identifying icon and other icon data, if any, may be based upon user input arising at approximately the time of outputting or at an earlier time. The identifying icon may be presented to the hub user prior to output thereof by the hub in the initial authentication signal. The display need not be included in the hub device and instead may be communicatively coupled thereto and provided by another device, such as by an external device or another IoT device which is already communicatively coupled to the hub.

In at least one embodiment, the initial authentication signal may include, in addition to at least the public key, data for use by the receiving IoT device(s) to generate one or more keywords, which may include a unique identifying keyword, for presentation to a user of the IoT device. For at least one embodiment, the keywords may be any configuration of alphanumeric characters. The keywords may be presented in any language, typeface, character set, or combinations thereof. The keywords may be randomly generated by the hub. The identifying keyword may be selected by or presented to the hub user prior to outputting thereof by the hub in the initial authentication signal. In at least one embodiment, the unique identifying keyword may not be included in the initial authentication signal, but, is known to the IoT device user.

In at least one embodiment, the initial authentication signal may include, in addition to at least the public key, data for use by the receiving IoT device(s) to generate one or more sounds, which may include an identifying sound, for presentation to a user of the IoT device. Such sound(s) may include one or more spoken words, sequences of sounds, example, a Morris code pattern, or other audible sounds or sound patterns. Such sounds may be presentable to a user of an IoT device using a speaker, headphone, earbud, or other audible communication technology provided by such IoT device or coupled thereof. The sound(s) may be presented in any language, sequence, or otherwise. The sound(s) may be randomly generated by the hub. The identifying sound(s) may be selected by the user prior to outputting thereof by the hub in the initial authentication signal.

In at least one embodiment, the initial authentication signal may include, in addition to at least the public key, data for use by the receiving IoT device(s) to generate one or more vibrations, including an identifying vibration, for presentation to a user of the IoT device. Such vibration(s) may include one or more sequences, for example, a Morris code sequence, or other humanly perceptible vibration patterns. Such vibrations may be presentable to a user of an IoT device using known technologies. The one or more vibration(s) may be randomly generated by the hub. The identifying vibration(s) may be selected by and/or presented to the hub user prior to outputting thereof by the hub in the initial authentication signal.

Accordingly, it is to be appreciated that an initial authentication signal includes a cryptologic component, such as a public key or otherwise, and one or more perceptible components, such as the above discussed icon(s), keyword(s), sounds, patterns, vibrations, or otherwise.

For at least one embodiment, the outputting of the initial authentication signal may occur as a broadcast to any IoT device then connected to the hub. For at least one embodiment, the outputting of the initial authentication signal may occur as a multicast or simulcast to only those one or more IoT devices then communicatively coupled to the hub using one or more communications mediums. For example, an outputting of the initial authentication signal may be multicast to those IoT devices connected to the hub via near field communications, while such authentication signal is not output to those IoT devices connected to the hub via Bluetooth, WIFI or other longer-range protocols. For at least one embodiment, the outputting of the initial authentication signal may occur to only those one or more IoT devices supporting features or functions then desired by a user. For example, a user might instruct, verbally or otherwise, his/her hub to activate a streaming video service. The hub may determine which then connected IoT devices are both within a given range of the hub and can directly or indirectly provide the desired streaming video services, and further identify the communications protocols to use to output the initial authentication signal to such IoT devices.

Per Operation 310, IoT device(s), within range of the hub and using the communications protocol(s) used by the hub to output the initial authentication signal, receive the initial authentication signal. It is to be appreciated that multiple IoT devices may receive the initial authentication signal.

Per Operation 312, each IoT device receiving the initial authentication signal determines whether such device can process the cryptologic component and present the perceptible component(s) to the IoT device user. For example, an initial authentication signal including a public keyword, an icon and a verbal password as its perceptible components would be disregarded by an IoT device not having audible output capabilities. If the IoT device does not have the necessary output capabilities, the process ends (Operation 313). If the IoT device has the necessary output capabilities, the process continues with Operation 314. For at least one embodiment, an initial authentication signal may specify that how the perceptible components are output may vary by a receiving IoT device. For example, a keyword could be output visibly, audibly, by vibration and/or otherwise to an IoT device user.

Per Operation 314, for each IoT device receiving the initial authentication signal and having the capabilities needed to present the perceptible components, the process continues with presenting the perceptible components to the device user. For at least one embodiment, the presented perceptible components may include an identifying component, such as an identifying icon, keyword, sound, vibration or combination thereof, and other random/non-identifying perceptible components, such as other icons, keywords, sounds, vibrations or combinations thereof.

Per Operation 316, the device user selects the corresponding identifying perceptible component(s) and the IoT device communicates such selection back to the hub. For at least one embodiment, this communication utilizes the cryptologic component to encrypt the data and provide for data security. For at least one embodiment, identification of two or more perceptible components may be required, such as an identifying icon and an identifying password. It is to be appreciated that the device user desirably knows which perceptible components are identifying and non-identifying based upon such device user being either the same person as the hub user or in communication with the hub user by other mechanisms, such as by proximity, or by distant/remote connection (e.g., by telephone).

Per Operation 317, an identification of a user of the IoT device may occur and may be communicated as device user identifying data to the hub. As shown by the dashed lines, this identification may be optional and may occur prior to or after communication to the hub of the device user's perceptible component selections. Identification of the device user may include use of any known or later arising user identifiers such as fingerprint, password, pin, pattern, or otherwise. The identification of the device user may occur using the IoT device seeking authentication with the hub, using the hub itself, using a standalone device, such as a pin input terminal, or otherwise. For at least one embodiment, this communication utilizes the cryptologic component to encrypt the device user identifying data and provide for data security.

Per Operation 318, the hub receives a responsive message from the IoT device. The responsive message including the device user's perceptible component selections and, when used, device user identifying data. The hub decrypts the data provided in the received responsive message using the cryptologic components, such as a private key corresponding to the public key, and determines if such selections and user identifications, if any, are correct/as expected. It is to be appreciated that the determination of whether a user identification is correct/as expected can involve the use of pre-existing data stored and/or accessible by a hub and/or the use of user verification data services, such as those provided by FACEBOOK, GOOGLE, APPLE, AMAZON and other service providers.

Per Operation 319, an optional number of re-entries/retries of either and/or both of selection of the identifying perceptible components and/or the device user identification data may be permitted. If so, the hub sends a retry message to the IoT devices. (Operation 321) If a proper selection and/or identification of the device user does not occur within a given number of re-entries/retries (which may be zero), the hub communicates a failure message to the IoT devices (Operation 323) and the process ends (Operation 313).

Per Operation 320, when proper selections and, optional, device user identification information is received by the hub, the process continues with the hub communicating a success message back to the IoT device from which the proper selections and identification originated.

Per Operation 322, secure, authenticated communications ("session data") between the IoT device and the hub may occur using the cryptologic component, such as a public key, communicated by the hub in the initial authentication signal. The IoT device may be configured to store the cryptologic component for use during the then arising connection with the hub. The session data may include any form of data, requests for data, requests for connections with third party service providers, or otherwise. The session data may include and/or provide between the authenticated IoT device and the hub, or vice versa, payment information, personal information, user preferences, data protected by further data protection mechanisms, or otherwise. For at least one embodiment, the session data may include a request by the authenticated IoT device to establish a permanent connection with the hub. Such a request for a permanent connection may be self-actuating such that upon the hub coming into range of the authenticated IoT device, or vice versa, a secure connection is established using the cryptologic component communicated in the initial authentication signal. It is to be appreciated that the authenticated IoT device may be configured to include secure data storage for the public key for such an embodiment.

For at least one embodiment, during a session (defined herein as the time during which session data is communicated between a hub and an authenticated IoT device), requests by the authenticated IoT device for the hub to provide data to or perform one or more operations on behalf of the IoT device may require approval by the hub user. For example, upon receipt of a request by the authenticated IoT device for the hub to provide certain data, the hub may be configured to notify the hub user, for example, via an audible tone or a vibration, and await approval by the hub user of the request. The approval may occur, for example, by a spoken command from the hub user, by a button selection on the hub, by a shaking of the hub, or otherwise.

Per Operation 324, at some point in time the session will end. It is to be appreciated, that the session may end upon completion of a desired transaction, for example, the end of a streaming video, after an elapse of time, after a period in which no further communications between the authenticated IoT device and the hub are received, or otherwise.

Per Operation 326, at the end of the current session, a determination is made by the hub as to whether the session is to be "permanent," such that the public key may be used later, or "temporary." If "temporary", the cryptologic component, such as a public key, is erased in both the hub and the IoT device. Any later desired connections between the IoT device and the hub will then proceed anew at Operation 300. It the session is deemed to be "permanent," the process continues with the next time the hub and the authenticated IoT device are within range and the IoT device requests services from the hub, as per Operation 330. That is, upon the authenticated requesting services from the hub the connection is again established, and communications proceed with the authenticated IoT device using the cryptologic component communicated in the initial authentication signal.

Per Operation 332, the process includes the verification that the cryptologic component, such as a public key, is still valid, and if so, the process continues with Operation 320. If the cryptologic component has expired or is not valid, the process continues with Operation 323.

Accordingly, it is to be appreciated that at least one embodiment of the present disclosure includes a process for authenticating an IoT device with a hub by use of a cryptologic component and a perceptible component, wherein each of these components are communicated by the hub to the IoT device and upon receipt of a valid responsive message back from an IoT device containing a selection of the perceptible component, the cryptologic component is utilized for further communications during a session. It is also to be appreciated that for at least one embodiment, a user identification may be utilized, in addition to the verification of a device user's selection of a perceptible component, to authenticate a session. It is further to be appreciated, that these processes may include the use of hardware and software, in the form of one or more computer executable instructions, in each of an IoT device and a hub. Such computer executable instructions, cryptologic component, perceptible components, and other data may be stored in computer readable mediums in a non-transient manner during a session, and for permanent sessions, in a non-transient manner after a given session.

Although various embodiments of the claimed invention have been described above with a certain degree of particularity, or with reference to one or more individual embodiments, those skilled in the art could make numerous alterations to the disclosed embodiments without departing from the spirit or scope of the claimed invention. The use of the terms "approximately" or "substantially" means that a value of an element has a parameter that is expected to be close to a stated value or position. However, as is well known in the art, there may be minor variations that prevent the values from being exactly as stated. Accordingly, anticipated variances, such as 10% differences, are reasonable variances that a person having ordinary skill in the art would expect and know are acceptable relative to a stated or ideal goal for one or more embodiments of the present disclosure. It is also to be appreciated that the terms "top" and "bottom", "left" and "right", "up" or "down", "first", "second", "next", "last", "before", "after", and other similar terms are used for description and ease of reference purposes only and are not intended to be limiting to any orientation or configuration of any elements or sequences of operations for the various embodiments of the present disclosure. Further, the terms "coupled", "connected" or otherwise are not intended to limit such interactions and communication of signals between two or more devices, systems, components or otherwise to direct interactions; indirect couplings and connections may also occur. Further, the terms "and" and "or" are not intended to be used in a limiting or expansive nature and cover any possible range of combinations of elements and operations of an embodiment of the present disclosure. Other embodiments are therefore contemplated. It is intended that all matter contained in the above description and shown in the accompanying drawings shall be interpreted as illustrative only of embodiments and not limiting. Changes in detail or structure may be made without departing from the basic elements of the invention as defined in the following claims.

What is claimed is:

1. A process for authenticating an IoT device with a hub to initiate an authenticated session, comprising:
    establishing an electronic data connection between an IoT device and a hub;
    sending, by the hub, an initial authentication signal;
        wherein the initial authentication signal includes a cryptologic component and at least two perceptible components;
            wherein the cryptological component includes a public key of a public key-private key keychain;
        wherein at least one of the at least two perceptible components is a randomly generated identifying perceptible component; and
        wherein the randomly generated identifying perceptible component includes at least two icons;
    receiving, by the hub, a responsive message;
        wherein the responsive message is secured, prior to transmission by the IoT device, by the cryptologic component by the private key for the public key-private key keychain; and
        wherein the responsive message includes a selection of a unique identifying icon selected from at least two icons of the randomly generated identifying perceptible component, and a unique identifying keyword;
    determining, by the hub, whether the selection includes the randomly generated identifying perceptible component; and
    if the result of the determining step is affirmative, establishing an authenticated session between the hub and the IoT device.

2. The process of claim 1,
wherein the establishing of the electronic data connection includes a Bluetooth pairing of the IoT device with the hub.

3. The process of claim 1,
wherein the randomly generated identifying perceptible component includes at least one of a keyword, a sound, and a vibration.

4. The process of claim 1,
wherein the unique identifying keyword is communicated to the IoT device in the initial authentication signal.

5. The process of claim 1, comprising:
receiving device user identifying data;
    wherein the device user identifying data identifies an intended user of the IoT device for a session; and
determining whether the intended user is authorized for the session.

6. The process of claim 5,
wherein the determining of whether the intended user is authorized for the session comprises contacting a user verification data service.

7. The process of claim 5,
where the user identifying data is secured, prior to transmission by the IoT device, using the cryptologic component.

8. The process of claim 1, comprising:
providing, during the authenticated session, a communications link connecting the IoT device with a third-party service provider;
    wherein upon establishment of the communications link, data can be communicated between the third-party service provider and the IoT device.

9. The process of claim 8,
wherein the data is communicated between the third-party service provider via a device link between the hub and the IoT device and a hub link between the hub and the third-party service provider; and wherein the authenticated session uses the device link.

10. The process of claim 9,
wherein the third-party service provider comprises at least one of a web services provider, a streaming service provider, and a data service provider.

11. The process of claim 10, comprising
establishing a second hub link between the hub and a second third-party service provider; and
establishing a second device link between the IoT device and the hub;
wherein the second device link facilitates a second authenticated session.

12. A hub device, for use in establishing an authenticated session with an IoT device, comprising:
a processor configured to execute computer readable instructions for establishing an authenticated session between the hub device and an IoT device;
an input/output module, coupled to the processor;
a security module, coupled to the processor;
a communications module, coupled to the processor;
a storage module, coupled to the processor, configured to store the computer readable instructions;
wherein the computer readable instructions include the operations of:
  establishing, via the communications module, an electronic data connection between an IoT device and the hub device;
  sending, via the communications module, an initial authentication signal;
    wherein the initial authentication signal includes a cryptologic component generated by the security module and a randomly generated identifying perceptible component;
      wherein the cryptological component includes a public key of a public key-private key keychain;
      wherein the randomly generated identifying perceptible component includes at least two icons;
  receiving, via the communications module, a responsive message;
    wherein the responsive message is secured, prior to transmission by the IoT device, by using the private key for the public key-private key keychain of the cryptologic component; and
    wherein the responsive message includes a selection of a unique identifying icon selected from the at least two icons of the randomly generated identifying perceptible component and a unique identifying keyword;
  decrypting, using the security module, the responsive message; and
  determining, by the processor, whether the selection includes the randomly generated identifying perceptible component; and
  if the result of the determining step is affirmative,
    establishing an authenticated session between the hub device and the IoT device; and
    outputting, using the input/output module, a humanly perceptible signal indicating the authenticated session is established.

13. The device of claim 12, comprising:
a coupling module configured to couple an external device to the hub device.

14. The device of claim 13,
wherein the external device is coupled to the hub device using at least one of physical coupling, magnetic coupling, inductive coupling, electrical coupling, and electro-optical coupling.

15. The system of claim 14,
wherein the external device comprises at least one of a power source, a second input/output module, a mapping module, a streaming module, a second processing module, a second data storage module, a sensing module.

16. The system of claim 14, comprising:
a position module, coupled to the processor, and configured to determine a position of the hub device.

17. The system of claim 16, comprising:
a sensor module, coupled to the processor, and configured to monitor at least one biometric for a user of the hub device and output at least one sensed signal indicative of the monitored biometric;
wherein the computer readable instructions comprise:
  receiving, from the sensor module, at least one sensed signal;
  analyzing the at least one sensed signal for an emergency medical condition; and
  upon detection of an emergency medical condition:
    obtaining, from the position module, a current position for the hub device;
    establishing, using the communications module, a communications link with a first-responder; and
    communicating to the first-responder the current position, and the at least one sensed signal.

18. A non-transitory processor-readable medium providing processor-readable instructions configured to cause one or more processors to execute an application program for use in establishing an authenticated session between a hub and an IoT device, wherein the processor-readable instructions comprise instructions for execution by a processor in an IoT device, comprising:
establishing an electronic data connection between the IoT device and the hub;
receiving from the hub an initial authentication signal;
  wherein the initial authentication signal includes a cryptologic component and at least two perceptible components;
    wherein the cryptological component includes a public key of a public key—private key keychain;
  wherein at least one of the at least two perceptible components is a randomly generated identifying perceptible component;
    wherein the randomly generated identifying perceptible component includes at least two icons;
outputting a responsive message secured by the private key of the cryptologic component and including a selection, by a user of the IoT device, of the randomly generated identifying perceptible component; and
upon a determination by the hub that the responsive message includes a selection of a unique identifying icon selected from at least two icons of the randomly generated identifying perceptible component and a unique identifying keyword, and an establishment of an authenticated session between the hub and the IoT device;
  requesting session data from at least one of the hub and a third-party service provider via the authenticated session between the hub and the IoT device;
    wherein the session data includes data provided by at least one of a streaming video service provider, a web service provider, and a data service provider.

* * * * *